(12) United States Patent
Jackson

(10) Patent No.: US 6,726,687 B2
(45) Date of Patent: Apr. 27, 2004

(54) CLOSURE PLUG FOR OPEN-HEADED MEDICAL IMPLANT

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 377 days.

(21) Appl. No.: 10/014,434

(22) Filed: Nov. 9, 2001

(65) Prior Publication Data

US 2002/0072751 A1 Jun. 13, 2002

Related U.S. Application Data

(63) Continuation-in-part of application No. 09/732,528, filed on Dec. 8, 2000, now Pat. No. 6,454,772.

(51) Int. Cl.[7] ............................................... A61B 17/58
(52) U.S. Cl. ........................................... 606/61; 606/73
(58) Field of Search ................................. 411/2–5, 383, 411/405; 606/72, 73, 61, 54, 55, 56, 57, 104; 52/584.1; D8/387; 473/336; 285/3; 184/105.3

(56) References Cited

U.S. PATENT DOCUMENTS

| 791,548 A | 6/1905 | Fischer |
|---|---|---|
| 1,300,275 A | 4/1919 | Johnson |
| 2,201,087 A | 5/1940 | Hallowell |
| 2,239,352 A | 4/1941 | Cherry |
| 2,295,314 A | 9/1942 | Whitney |
| 2,532,815 A | 12/1950 | Kindsvatter |
| 2,553,337 A | 5/1951 | Shafer |
| 2,778,265 A | 1/1957 | Brown |
| 2,877,681 A | 3/1959 | Brown |
| 2,927,332 A | 3/1960 | Moore |
| 3,143,029 A | 8/1964 | Brown |
| D200,217 S | 2/1965 | Curtiss |
| 3,370,341 A | 2/1968 | Allsop |
| 3,498,174 A | 3/1970 | Schuster et al. |
| 3,584,667 A | 6/1971 | Reiland |
| 3,812,757 A | 5/1974 | Reiland |

(List continued on next page.)

FOREIGN PATENT DOCUMENTS

| DE | 3630863 | 3/1988 |
|---|---|---|
| DE | 373809 | 5/1989 |
| EP | 195455 | 9/1986 |
| EP | 172130 | 2/1987 |
| EP | 276153 | 7/1988 |
| EP | 465158 | 1/1993 |
| FR | 2467312 | 4/1981 |
| GB | 203508 | 9/1923 |
| GB | 2082709 | 3/1982 |
| WO | PCT92/03100 | 3/1992 |
| WO | PCT94/10927 | 5/1994 |
| WO | PCT94/10944 | 5/1994 |
| WO | PCT96/06576 | 3/1996 |

OTHER PUBLICATIONS

Two Drawings of Sofamor dated Mar. 10, 1994 and Sep. 20, 1994.

*Primary Examiner*—Julian W. Woo
(74) *Attorney, Agent, or Firm*—John C. McMahon

(57) ABSTRACT

A closure for an open headed medical implant, such as a bone screw. The closure having a cylindrical body having an axis of rotation and also having a threaded radially outer surface. The body having a plurality of bores that open onto a top surface of the body and that are parallel to but spaced from the axis of rotation. In one embodiment the closure also has a break-off head centrally attached by a neck to the top surface of the body. Preferably, the body also includes an axial threaded bore that extends from a bottom to the top of the surface body, but that is only exposed when the break-off head breaks away. In another embodiment a tool is used to insert the closure in the implant without a break-off head and a central threaded bore of the closure receives a set screw.

13 Claims, 5 Drawing Sheets

U.S. PATENT DOCUMENTS

| | | | |
|---|---|---|---|
| 3,963,322 A | 6/1976 | Cryctko | |
| 4,269,246 A | 5/1981 | Larson et al. | |
| 4,492,500 A | 1/1985 | Ewing | |
| 4,506,917 A | 3/1985 | Hansen Arne | |
| 4,577,448 A * | 3/1986 | Howorth | 52/584.1 |
| 4,641,636 A | 2/1987 | Cotrel | |
| 4,763,644 A | 8/1988 | Webb | |
| 4,764,068 A | 8/1988 | Crispell | |
| 4,790,297 A | 12/1988 | Luque | |
| 4,815,453 A | 3/1989 | Cotrel | |
| 4,838,264 A | 6/1989 | Bremer et al. | |
| 5,005,562 A | 4/1991 | Cotrel | |
| 5,026,373 A | 6/1991 | Ray et al. | |
| 5,067,955 A | 11/1991 | Cotrel | |
| 5,073,074 A | 12/1991 | Corrigan et al. | |
| 5,129,388 A | 7/1992 | Vignaud et al. | |
| 5,147,360 A | 9/1992 | Dubousset | |
| 5,154,719 A | 10/1992 | Cotrel | |
| 5,261,907 A | 11/1993 | Vignaud et al. | |
| 5,261,912 A | 11/1993 | Frigg | |
| 5,282,707 A | 2/1994 | Palm | |
| 5,312,404 A | 5/1994 | Asher et al. | |
| 5,334,203 A * | 8/1994 | Wagner | 606/61 |
| 5,346,493 A | 9/1994 | Stahurski et al. | |
| 5,364,400 A | 11/1994 | Rego, Jr. et al. | |
| 5,382,248 A | 1/1995 | Jacobson et al. | |
| 5,385,583 A | 1/1995 | Cotrel | |
| 5,387,212 A * | 2/1995 | Yuan et al. | 606/61 |
| 5,487,742 A | 1/1996 | Cotrel | |
| 5,496,321 A | 3/1996 | Puno et al. | |
| 5,499,892 A | 3/1996 | Reed | |
| 5,507,747 A | 4/1996 | Yuan et al. | |
| 5,562,663 A | 10/1996 | Wisnewski et al. | |
| 5,591,235 A | 1/1997 | Kuslich | |
| 5,630,817 A | 5/1997 | Rokegem et al. | |
| 5,643,260 A | 7/1997 | Doherty | |
| 5,653,710 A | 8/1997 | Harle | |
| 5,697,929 A | 12/1997 | Mellinger | |
| D407,302 S * | 3/1999 | Lawson | D8/387 |
| 5,879,350 A | 3/1999 | Sherman et al. | |
| 6,149,533 A * | 11/2000 | Finn | 473/336 |
| 6,193,719 B1 | 2/2001 | Gournay et al. | |
| 6,224,598 B1 | 5/2001 | Jackson | |
| 6,322,108 B1 * | 11/2001 | Riesselmann et al. | 285/3 |
| 6,349,794 B2 * | 2/2002 | Spencer | 184/105.3 |

* cited by examiner

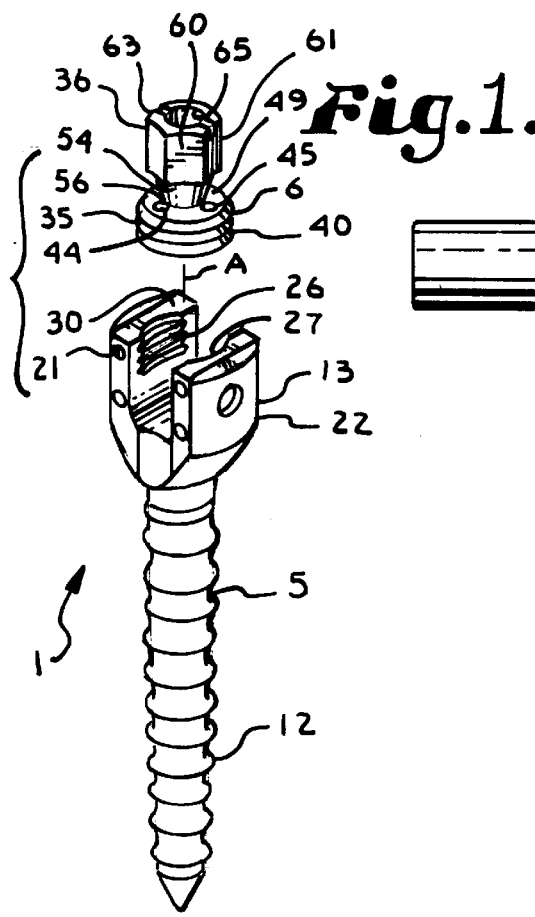
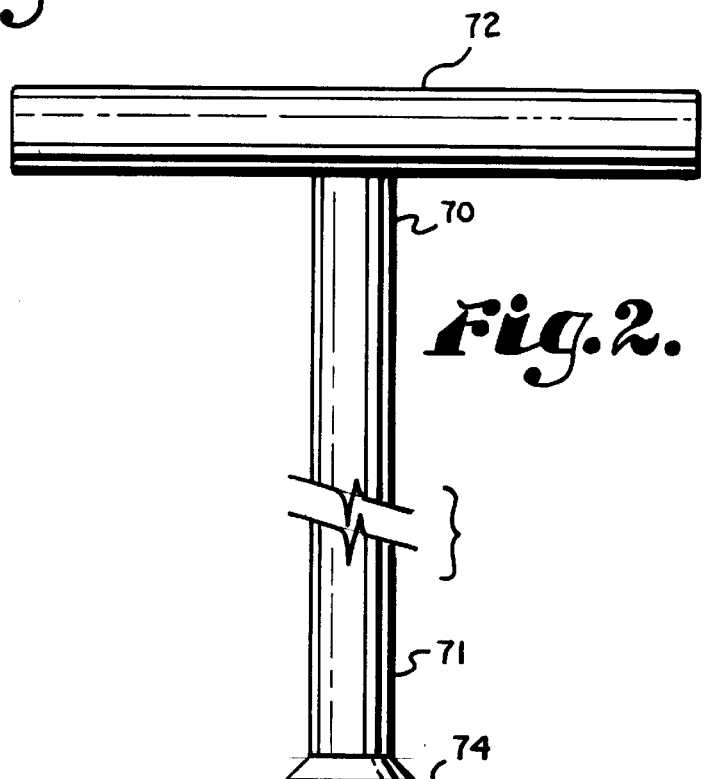
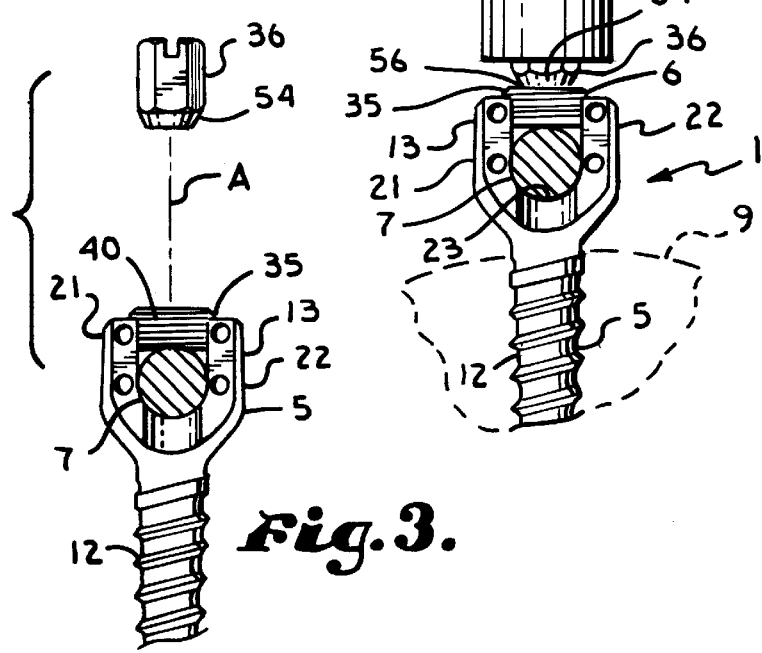
Fig.1.
Fig.2.
Fig.3.

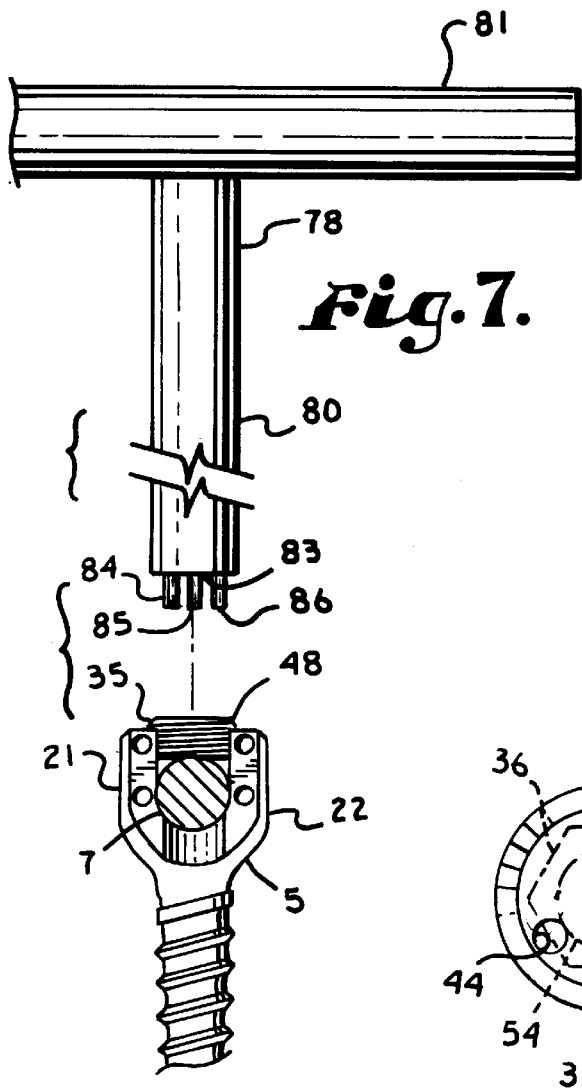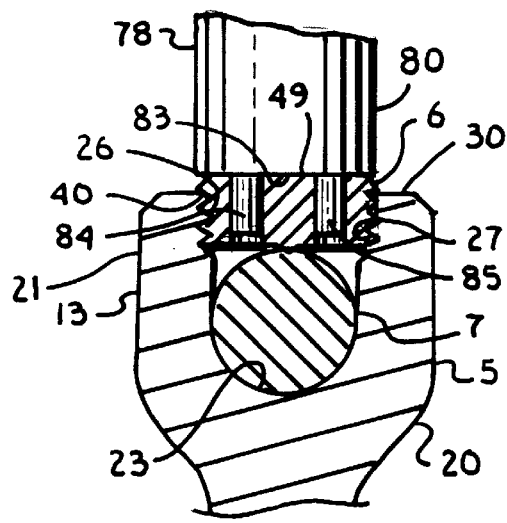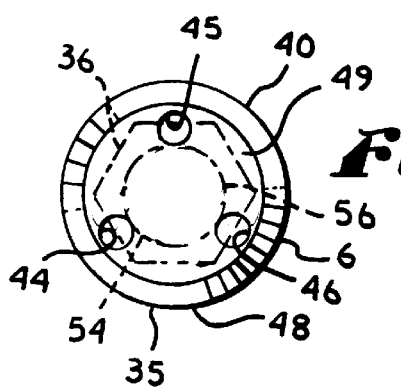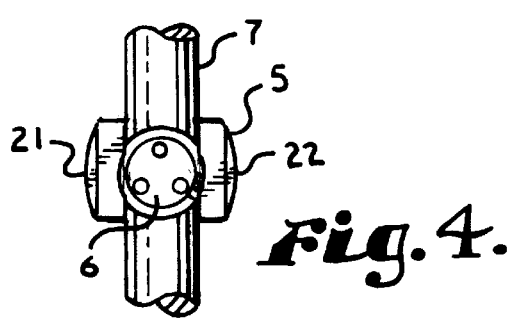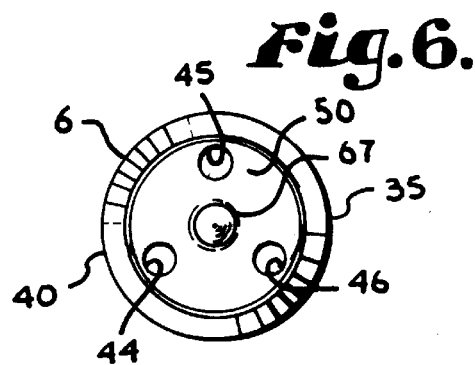

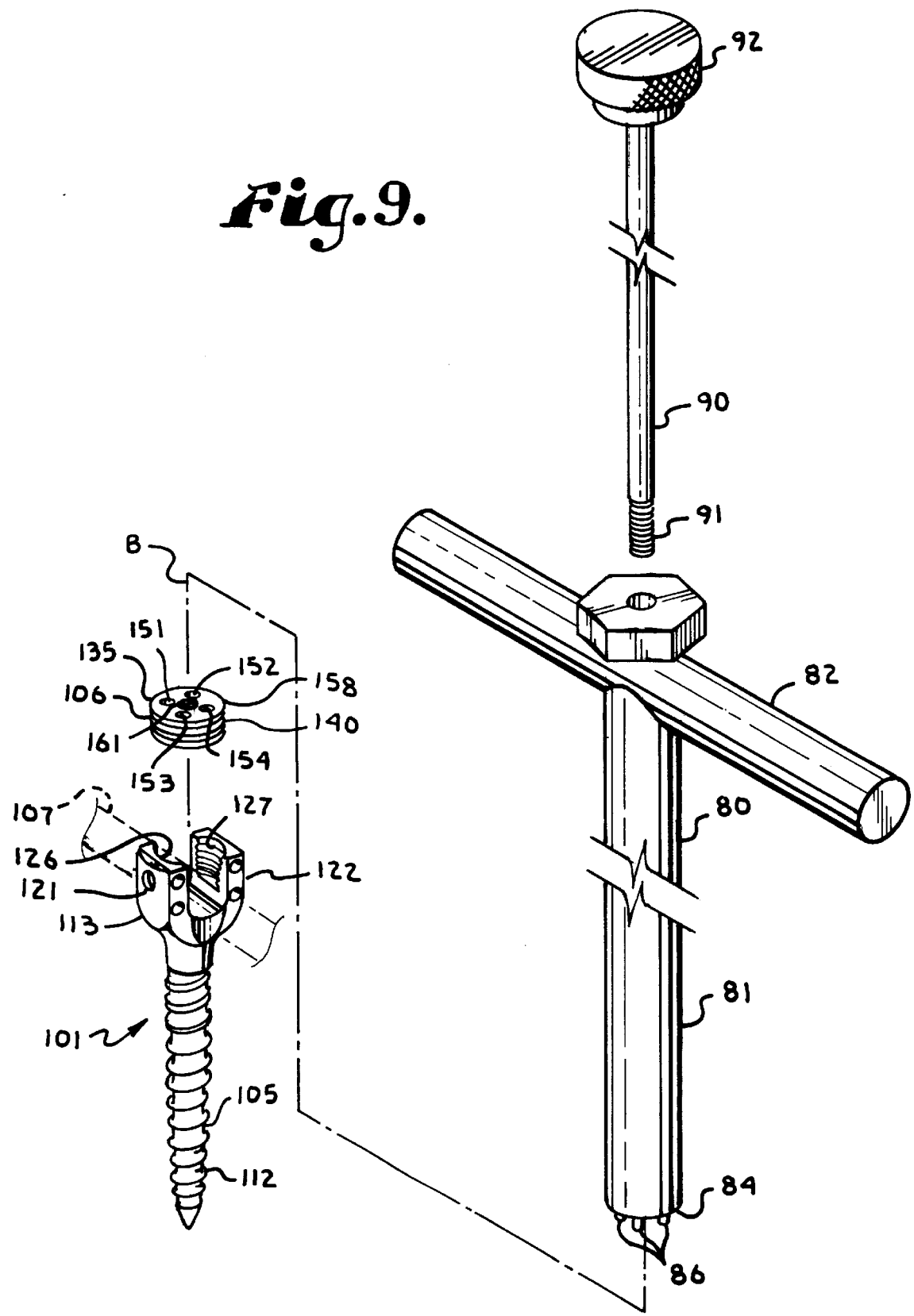

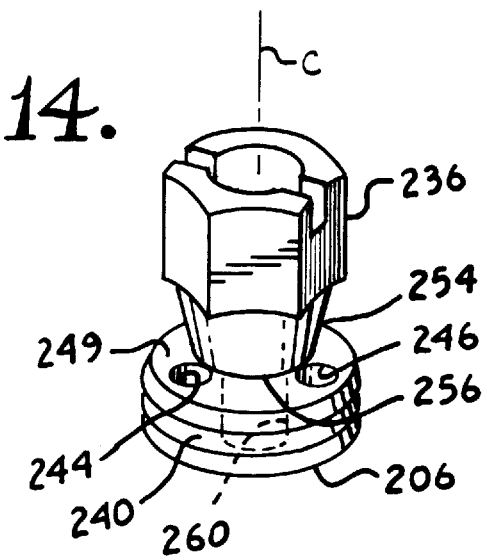
*Fig.*14.
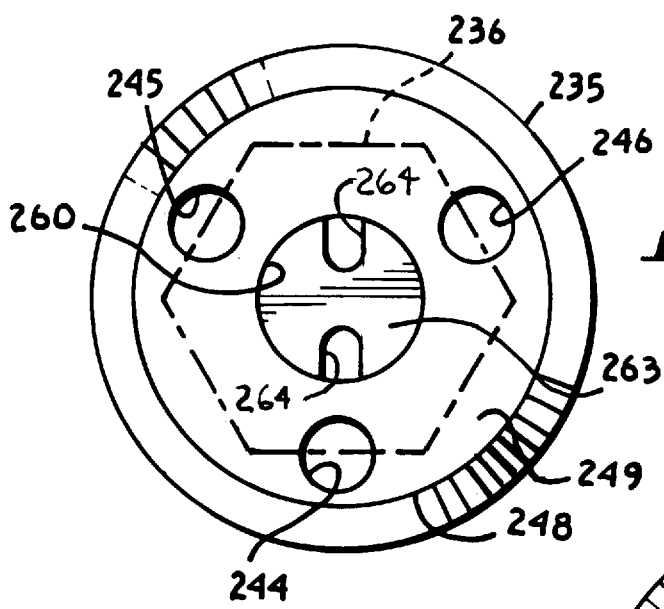
*Fig.*15.
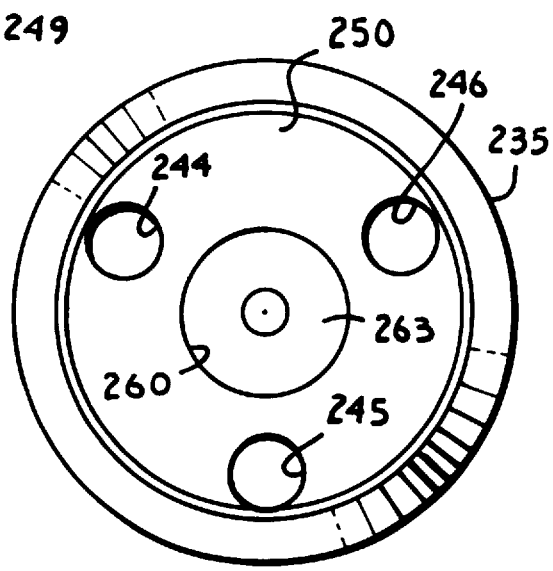
*Fig.*16.

CLOSURE PLUG FOR OPEN-HEADED MEDICAL IMPLANT

BACKGROUND OF THE INVENTION

The present invention is directed to an open headed medical implant and, in particular, to a closure for closing the head of an open headed bone screw, hook or the like.

Bone screws are used especially in spinal surgery to support and position various implants needed to repair a spine that has suffered injury, illness or genetic defect. Bone screws of this type are screwed into the vertebrae of the spine and have a head that projects outside the bone which receives other implants, such as rods, that extend along the spine. Bone screws are of two general types which are either open headed or closed headed. Hooks and certain other implants also sometimes have open heads. The present application is directed to open headed bone screws and related implants such as hooks and the like that have such an open head to receive another implant.

In open headed bone screws and related implants, the head includes two upright arms that form a channel therebetween. The channel is sized to receive a rod or the like and is open to make it easier to place the rod in the head. The rod must then be tightly held or locked in the head to prevent relative movement between implants after the surgery. To hold the rod in the head, plugs have been used that are screwed into threads on the interior surfaces of the arms.

The present invention is directed especially to improvements in such plugs or closures that make them easier to insert in the head, that better ensure that the plug effectively secures the rod so that the rod does not later slip, that allow the plugs to be easily removed should the overall implant system require rearrangement and which provide a comparatively low profile, so as reduce trauma and irritation to the surrounding tissues of the patient.

SUMMARY OF THE INVENTION

A closure is provided for an open headed implant, especially a bone screw or hook for use in spinal surgery. The closure has a cylindrical shaped body with an axis of rotation. The body has a radially outer surface that is threaded with a thread that is sized and shaped to be received in mating threads on interior surfaces of arms of the implant head. The closure is operably threaded into the head of the implant to capture a rod or other part of an overall spinal support system. The closure captures and locks such a rod in position relative to the implant to prevent rotation or axial movement between the joined parts.

The closure body has a top surface and a bottom surface with a plurality of bores extending parallel to the axis of rotation into the body from the top surface. The bores are positioned in spaced relationship to one another and to the axis of rotation. The bores are sized and shaped to cooperatively mate with posts on a tool to allow removal of the closure from the implant after insertion, should such be necessary. In some instances the tool may also be used to install the closure in the implant.

In one embodiment the closure also includes a break-off head centrally mounted by a neck on the top surface of the body. The break-off head is adapted to receive a socket tool and be rotated thereby during installation. The break-off head is also designed to break from the body at a break-off point or location which is preferably whereat the neck intersects with the top surface of the body; when a preselected torque is applied to the break-off head. When the break-off head is broken away, the bores that are adapted to mate with a removal tool become exposed.

In a second embodiment the body includes a central threaded bore that receives a set screw. The body is then used for capture of a rod or the like and the set screw is used to lock the rod or the like in position relative to the implant.

In a third embodiment, a body includes both a break-off head and a central threaded bore that is covered by the break-off head until the head breaks away, after which the threaded bore is exposed at the top surface of the body to receive a set screw.

OBJECTS AND ADVANTAGES OF THE INVENTION

Therefore, the objects of the present invention are: to provide a closure for an open ended implant that provides a plurality of spaced bores that are offset from an axis of rotation of the closure and that cooperate with a tool to allow removal of the closure; to provide such an implant having a closure with a break off head for mating with an insertion tool for inserting the closure into the implant; to provide such an implant wherein the removal bores are not accessible for effective access, when the closure is in the implant until the break-off head is broken away; to provide such an implant having a closure wherein a closure body has an axially centered threaded bore and including a set screw sized and shaped to be threaded into and extend from the bottom of the closure threaded bore when fully inserted therein; to provide such an implant having a break-off head joined by a neck to a body of the closure and centered on a top of the closure with the body also having a central threaded bore that extends from a bottom to the top of the closure body, but the threaded bore is unaccessible at the top of the body until the break-off head breaks from the body; to provide such an implant that strongly grips a rod or the like received in the implant and that provides a relatively low profile; and to provide such an implant and closure therefore that is relatively easy to use, comparatively easy to produce and is especially well suited for the intended use thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a bone screw type implant and closure cap in accordance with the present invention prior to insertion of the closure cap into a head of the bone screw.

FIG. 2 is a fragmentary side elevational view of the bone screw with a rod and the closure received therein and with a tool being utilized to insert the closure and provide torque to the break-off head of the closure and further with the bone screw shown embedded in a bone that is indicated by phantom lines.

FIG. 3 is a fragmentary and exploded side elevational view of the bone screw, rod and closure with the break-off head of the closure being shown broken therefrom.

FIG. 4 is a fragmentary top plan view of the bone screw, rod and closure with the break-off head removed.

FIG. 5 is a top plan view of the closure with the break-off head broken therefrom, but shown in phantom.

FIG. 6 is a bottom plan view of the closure.

FIG. 7 is an exploded and fragmentary side elevational view of the bone screw, rod and closure showing a removal tool positioned above the closure.

FIG. 8 is a fragmentary and enlarged view of the bone screw, rod and closure shown in FIG. 7 with the removal tool inserted into the closure and with portions of the bone screw and closure broken away to show detail thereof.

FIG. 9 is an exploded perspective view of a modified bone screw and closure in accordance with the present invention, also showing a rod received in a head of the bone screw in phantom lines and a tool for use in inserting the closure into and removing the closure from the head of the bone screw.

FIG. 14 is a side elevational view of a closure in accordance with a second modified embodiment of the present invention.

FIG. 15 is a top plan view of the closure of the second modified embodiment with a break-off head thereof broken away.

FIG. 16 is a bottom plan view of the closure of the second modified embodiment of the invention.

DETAILED DESCRIPTION OF THE INVENTION

Figure 10:
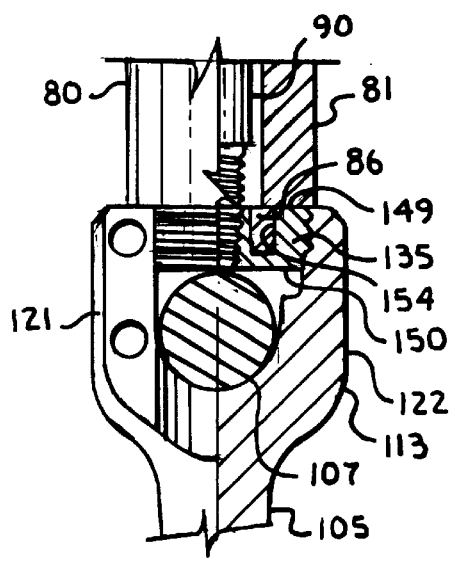
FIG. 10 is a side elevational view of the bone screw, rod, closure and tool of the second embodiment of the invention with portions broken away to show internal detail thereof.
Figure 11:
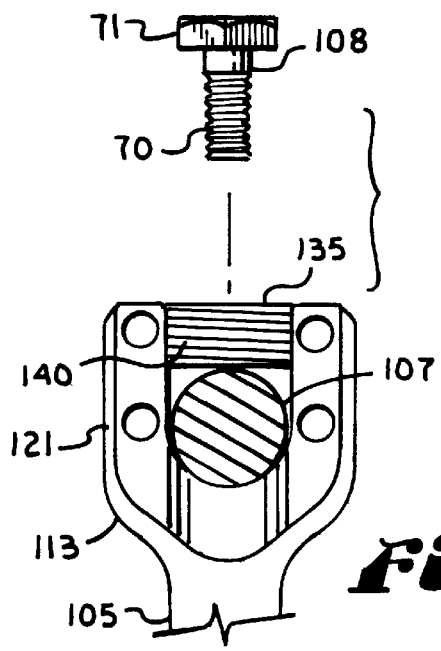
FIG. 11 is a fragmentary side elevational view of the bone screw, rod and closure also showing a set screw that is positioned to be received in the closure.
Figure 12:
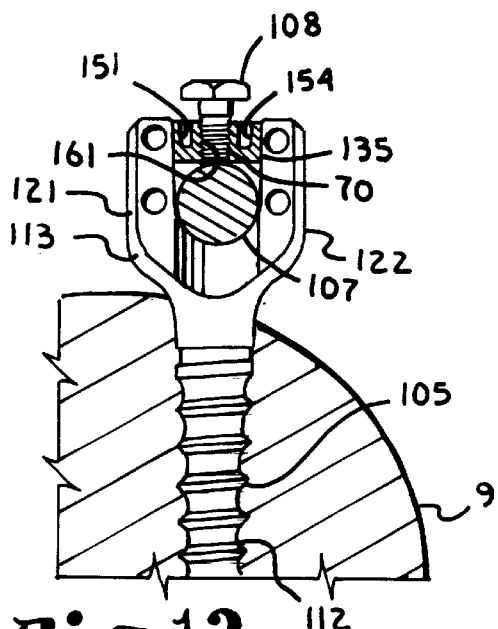
FIG. 12 is a fragmentary side elevational view showing the bone screw, rod, closure and closure set screw positioned in a vertebrae that is shown in cross-section.
Figure 13:
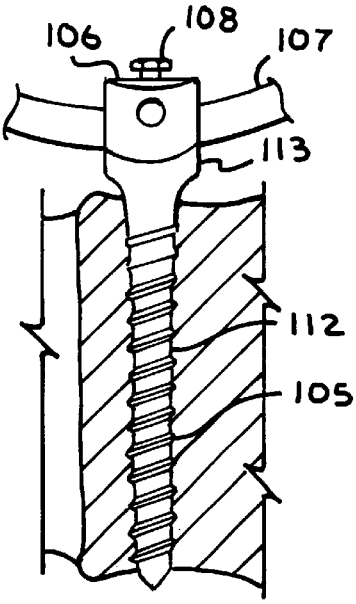
FIG. 13 is a front elevational view of the bone screw, rod and closure shown mounted in a vertebrae that is shown in cross-section.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a first embodiment of a medical implant in accordance with the present invention which is shown in FIGS. 1 to 8. The implant 1 includes a bone screw 5, a closure 6 for the bone screw and a rod 7. The implant is received in a vertebrae 9, typically in conjunction with other implants that are not shown. The closure 6 also functions in conjunction with other open-headed implants, such as hooks and the like.

The bone screw 5 includes a shank 12 and a head 13. The shank 12 is threaded with a coarse flighting-like thread 16 that is threaded into the vertebrae 9 so as to secure and support the bone screw 5 and allow the head 13 to extend from the vertebrae 9.

The bone screw head 13 includes a base 20 with a pair of upstanding spaced arms 21 and 22 on opposite sides of the base 20 forming a generally U-shaped configuration when viewed from the side and defining a channel 23 therebetween. The channel 23 is sized and shaped to receive the rod 7.

The arms 21 and 22 each include an interior threaded surface 26 and 27 respectively. The threaded surfaces 26 and 27 are spaced and not connected so as to present only a partial threadform which each face one another and cooperate with the closure 6, as is noted below. In the illustrated embodiment, the threaded surfaces 26 and 27 extend from a top 30 of the bone screw only partially down the arms 21 and 22.

The closure 6 includes a body 35 and a break-off head 36. In the present embodiment shown in FIGS. 1 through 8 the closure body 35 is generally cylindrical in shape and has a radially outward external threaded surface 40 that extends 360° about an axis of rotation indicated by the reference letter "A". That is, the threaded surface has a threadform located thereon that entirely encircles the outer threaded surface 40 of the body 35 and extends entirely from top to bottom. The threaded surface 40 is provided with a thread that is sized, shaped and configured to rotatably mate with the threaded surfaces 26 and 27 of the arms 21 and 22, so that the closure body 35 may be threaded into the bone screw head, as is shown in FIG. 2.

The closure body 35 also includes three bores 44, 45 and 46 that are aligned to be parallel with the axis of rotation. The bores 44, 45 and 46 are spaced both from the axis of rotation A and from a periphery 48 of a top 49 of the body. The bores 44, 45 and 46 extend from the body top 49 to a bottom surface 50 of the body 35 in the present embodiment. Preferably the bores 44, 45 and 46 are equally spaced from one another and are approximately equally radially spaced outward from the axis of rotation A. In the embodiment illustrated in FIGS. 1 through 8, the bores 44, 45 and 46 are spaced at approximately 120° from one another.

The break-off head 36 includes a neck 54 that joins with the body top 49 at a break-off location 56. Preferably the break-off location 56 is generally coplanar with the body top 49, so the break-off is clean and low profile. The break-off location is normally determined by the location whereat the neck 54 is smallest in cross-section or can be triggered by an external groove. The neck 54 also converges somewhat from the remainder of the break-off head 36 to the break-off location 56.

The break-off head 36 includes a number of facets or panels which are aligned to be parallel to the axis of rotation A and which are joined together to form a polyhedral shape typically associated with a structure to be received in a socket-type tool. A combined surface 61 of the facets 60 forms such a polyhedral shape. A top surface 63 of the break-off head 36 has axially located therein a non-threaded bore 65 for operably receiving a tool during implantation. The bottom surface 50 of the body 35 includes a conical shaped and axially aligned point 67.

A tool 70 is illustrated in FIG. 2 for cooperatively inserting the closure 6 into the bone screw head 13. The tool 70 has an elongate shank 71 with a handle 72 sized and shaped to allow a user to rotate the tool 70 clockwise about the axis of rotation A associated with the closure 6. The tool 70 also has a socket type head 74 opposite the handle 72 that is sized and shaped to snugly receive the outer surface 61 of the break off head 36 as is shown in FIG. 2.

During assembly, the rod 7 which is elongate and generally circular in cross-section is placed within the bone screw channel 23 and the closure 6 is then threaded into the bone screw head 13. The tool 70 is used to rotate the closure 6 until it engages the rod 7 and urges the rod 7 to seat tightly and snugly on the bone screw head base 20 at the bottom of the channel 23. The point 67 engages and digs into the rod 7. As additional torque is applied to the tool 70, a preselected torque is eventually reached (for example 90 inch pounds) where the break-off head 36 breaks from the closure body 35 at the break-off location 56 and separates therefrom, such as is shown in FIG. 3.

FIGS. 3 and 4 illustrate the closure 6 operably positioned within the bone screw head 13. FIG. 5 illustrates the closure 6 with the break-off head 36 removed, but shown in phantom to illustrate the position of the break-off head 36 relative to the bores 44, 45 and 46.

In certain circumstances, it is necessary to remove the closure 6 to readjust the position of the rod 7 or to make some other change in the implant configuration. As mentioned before, the implant 1 is typically a part of an overall system and is normally used to provide support to damaged, injured or missing vertebra of the spinal column. When it is necessary to readjust the system, the closure 6 is removed by utilization of the second tool 78. The tool 78 includes a shank 80 that has an axis of rotation during use that is coaxial with the axis of rotation A of the closure 6. The shank 80 is attached at one end to a handle 81 to provide a grasp and a means of turning the tool 78 by user. Opposite the handle 81, the shank 80 has a flat surface 83 from which three pegs or posts 84, 85 and 86 project. The posts 84, 85 and 86 are parallel to the axis of rotation of the tool 78 and are sized, shaped and positioned so as to be snugly receivable in the closure bores 44, 45 and 46, subsequent to removal of the break-off head 36. The tool 78 is shown in position above the closure body 35 in FIG. 7 just prior to insertion of the posts 84, 85 and 86 into respective bores 44, 45 and 46. The tool 78 is shown positioned with the posts 84, 85 and 86 in the respective bores 44, 45 and 46 in FIG. 8. The purpose of the tool 70 is to allow user to rotate the closure body 35 counter-clockwise and remove the body 35 from the bone screw head 13 after the closure 6 has been seated therein. In this way the channel 23 can be reopened and the rod 7 removed or repositioned relative to the bone screw head 13.

While the non-axially located bores 44, 45 and 46 of the present embodiment are located between the break-off head neck 54 and the periphery 48, it is foreseen that one or more non-axial bores of this type could partially or entirely intersect with the neck 54 so as to become fully open or exposed at the closure top surface 49 only when a break-off head associated with such a neck breaks from the closure body.

Illustrated in FIGS. 9 to 13 is second embodiment or first modified embodiment of an implant in accordance with the present invention that is generally identified by the reference numeral 101. The implant 101 includes a bone screw 105, a closure 106, a rod 107 and a set screw 108.

The bone screw 105 except for the closure is essentially the same as the bone screw 5 and, therefore, will not be described in detail. Reference is made to the description of bone screw 5 for additional detail. The bone screw 105 has a shank 112 and a head 113. Upright arms 121 and 122 of the head 113 have inner or interior facing and threaded surfaces 126 and 127.

The rod 107 is elongate and has a generally circular cross section for being received in the head 113 beneath the closure 106.

The closure 106 is similar in some respects to the closure 6, but is installed in a different manner. In particular, the closure 106 has a generally cylindrical shaped body 135 that has a threaded radially outward surface 140 that has a thread thereon that is sized, shaped and positioned to threadedly mate with threads of the arm threaded surfaces 126 and 127, as seen in FIG. 10. The thread can be a conventional V-thread, a buttress thread, a reverse angle thread or other threads related to reverse angle threads in that they exert forces to draw or pull the arms 121 and 122 toward one another rather than cause them to splay or open at the top.

The body 135 also has a top surface 149 and a bottom surface 150. Positioned to extend downwardly into the body 135 form the top surface 149 are four equally spaced bores 151, 152, 153 and 154 that do not extend entirely through the body 135 from top to bottom. The bores 151, 152, 153 and 154 are spaced form and positioned between both a central axis B and a periphery 158 of the body top surface 149. Each bore 151, 152, 153 and 154 is positioned at approximately 90° relative to adjacent bores 151, 152, 153 and 154.

Located axially and centrally in the body 135 is a threaded bore 161. The threaded bore 161 extends between the top surface 149 and bottom surface 150.

The set screw 108 has a threaded shaft 170 sized and shaped to be threadably received in the body threaded bore 161. The set screw 170 has sufficient length to extend through and outward from the bottom surface 150. In the second embodiment the set screw 108 has a head 171 that is gripable by a tool for rotation and torquing.

A tool 180 is provided for installing and removing the closure 106 form the bone screw head 113. The tool 180 is T-shaped having a shank 181 with a handle 182 attached to one end and a generally flat surface 184 at an opposite end. The surface 184 has four pegs or posts 186 extending therefrom. The posts 186 extend form the surface 184 parallel to an axis of rotation of the tool 180 which is the same in use as the axis of rotation B of the closure. The posts 186 are aligned, sized and shaped to mate with the closure body bores 151, 152, 153 and 154.

The tool shank 170 also includes an axial bore extending therethrough and receiving a keeper rod 190. The rod 190 has a threaded tip 191 that is adapted to be received in the closure body bore 161 and a grasping head 192 at an opposite end.

In use the rod 107 is placed in the head 112 and the tool 180 is mated with the closure 106 in the manner shown in FIG. 10, so that the four posts 186 are located in respective bores 151, 152, 152 and 154 and the rod tip 191 is threaded into the threaded bore 161. The closure 106 is then mated with the head 112 and threaded thereon by mating of the surface 140 with the arm surfaces 126 and 127 until the closure 106 is snug in the bone screw head 113. Torque in a preselected amount is applied to the closure 106 to ensure it is tightly seated in the head 112. In some instances, the closure 106 may just be used to capture the rod 107 and the set screw 108 is used to lock the rod 107 in place. In particular, the tool 180 may be removed and the set screw 108 is then placed in the bore 161 and advanced against the rod 107. A preselected torque is applied to lock the rod 107 in a selected position in the head 112.

It is foreseen that the set screw 108 may be of other types than the one illustrated. That is the set screw could have a break-off head in which case the overall implant 101 would have a comparatively low profile associated with only the top of the bone screw.

For removal, the installation process is reversed. That is the tool 180 is utilized to rotate the closure 106 counter-clockwise rather than the clockwise direction used for inserting. Where a break off set screw is used, the set screw can be rotated with the body 135 of the closure 106 for removal.

Illustrated in FIGS. 14, 15 and 16 is a third embodiment or second modified embodiment of a bone screw closure in accordance with the present invention and generally identified by the reference numeral 206.

The closure 206 is in many ways similar to the closure 6 and reference is made to the disclosure for the closure 6 for additional detail.

In particular the closure 206 has a generally cylindrically shaped body 235 that has a radially outer threaded surface 240. The closure 235 also has a break-off head 236 secured to a top or upper surface 249 of the body 235 by a neck 254 at a break-off location 256. Positioned between the neck 254 and a periphery 248 of the body upper surface 249 are three bores 244, 245 and 246 that extend parallel to a central axis of rotation identified by a reference numeral C.

The major difference between the present embodiment and the closure 6 shown in the first embodiment is that a body 235 thereof also includes a central or axial bore 260 extending from a bottom surface 250 upward through the body 235 to the level of an upper surface 249 of the body 235. The bore 260 is threaded and covered by the neck 254 until the break-off head 236 breaks form the body 235 during installation by application of torque, as was described in the first embodiment. The bore 260 is thereafter exposed upwardly or at the upper surface 249 and adapted to receive a set screw 263 of the type used in the second embodiment or alternatively a break-off type, as shown, set screw having removal slots 264. It is noted that the diameter of the neck 254 at the top surface 249 is larger than the diameter of the bore 260.

It is to be understood that while certain forms of the present invention have been illustrated and described herein, it is not to be limited to the specific forms or arrangement of parts described and shown.

What is claimed and desired to be secured by Letters Patent is as follows:

1. An open-headed medical implant having:
   a) a first element adapted to operably be joined to a bone or other implant;
   b) an implant head secured to said first element and having a pair of upright spaced arms defining a channel therebetween; said arms each having facing interior threaded surfaces;
   c) a plug for closing said channel between said arms; said plug comprising:
      i) a body sized and shaped to be received between the arms of said head; said body having a radially outward surface that has a thread thereon that is sized and shaped to threadedly mate with the threaded arms of said head;
      ii) said body having a top and a bottom; said top of said body having at least one bore therein sized and shaped to receive a tool and extending generally axially at least partially through said body from top to bottom thereof; and wherein:
      iii) said bore is spaced from and positioned between both a central axis of said body and a periphery of said body.

2. The implant according to claim 1 wherein:
   a) there are a pair of spaced bores extending into said body from the top surface thereof.
3. The implant according to claim 1 wherein:
   a) said body is generally cylindrical in shape.
4. The implant according to claim 1 including:
   a) a break-off head joined to said body by a neck; said neck being aligned with the central axis of said body.
5. The implant according to claim 4 wherein:
   a) said body includes at least a pair of said bores in the top thereof; and
   b) said neck is positioned between said bores.
6. The implant according to claim 4 wherein:
   a) said break-off head has a tool gripable outer surface for operably rotating said closure during insertion into said implant head and said neck being sized and shaped such that said break-off head breaks from said body when a preselected torque is applied to said break-off head by such a gripping tool with a generally clean profile at said top surface.
7. The implant according to claim 4 wherein:
   a) said body includes an axial extending bore from the bottom to near the top thereof; said axial bore being located beneath said neck and being accessible from the top of said body when said break-off head breaks away from said body.
8. The implant according to claim 7 wherein:
   a) said axial bore is threaded.
9. The implant according to claim 1 wherein:
   a) said closure includes an axial threaded bore passing entirely through said body from a top to a bottom thereof.
10. The implant according to claim 9 in combination with:
    a) a threaded set screw sized and shaped to be received in said axial bore; said axial set screw being also sized and shaped to extend outward from said body bottom surface when said screw is fully installed therein.
11. The implant according to claim 1 wherein:
    a) said body top surface has three spaced tool receiving bores located therein; each of said bores being located at a common radius from said body central axis and being spaced at 120° from adjacent tool receiving bores.
12. The implant according to claim 1 wherein:
    a) said body top has four spaced tool receiving bores each being located at a common radius from said body central axis and being evenly spaced from adjacent tool receiving bores.
13. The implant according to claim 1 including:
    a) a tool having a gripable handle and an engagement face; said face including a post extending parallel to an axis of rotation of said tool for each said body bore; each said post being sized, aligned and positional to simultaneously enter a respective bore so as to rotate and apply torque to said body when said tool is rotated about the axis thereof, whereby said tool is operable to at least remove said body from said implant head in which said body has been inserted.

* * * * *